United States Patent
Arba Mosquera et al.

(10) Patent No.: US 12,396,888 B2
(45) Date of Patent: Aug. 26, 2025

(54) METHOD FOR PROVIDING CONTROL DATA OF AN EYE SURGICAL LASER OF A TREATMENT APPARATUS BASED ON A PATIENT-SPECIFIC PARAMETER SET; CONTROL DEVICE AS WELL AS TREATMENT APPARATUS

(71) Applicant: SCHWIND eye-tech-solutions GmbH, Kleinostheim (DE)

(72) Inventors: Samuel Arba Mosquera, Aschaffenburg (DE); Shwetabh Verma, Aschaffenburg (DE)

(73) Assignee: SCHWIND eye-tech-solutions GmbH, Kleinostheim (DE)

( * ) Notice: Subject to any disclaimer, the term of this patent is extended or adjusted under 35 U.S.C. 154(b) by 320 days.

(21) Appl. No.: 17/562,185

(22) Filed: Dec. 27, 2021

(65) Prior Publication Data
US 2022/0218524 A1 Jul. 14, 2022

(30) Foreign Application Priority Data
Jan. 11, 2021 (DE) ...................... 10 2021 100 285.0

(51) Int. Cl.
*A61F 9/008* (2006.01)

(52) U.S. Cl.
CPC ...... *A61F 9/00802* (2013.01); *A61F 9/00825* (2013.01); *A61F 2009/00872* (2013.01);
(Continued)

(58) Field of Classification Search
CPC .............. A61F 9/00802; A61F 9/00825; A61F 2009/00872; A61F 2009/00878;
(Continued)

(56) References Cited

U.S. PATENT DOCUMENTS

| | | |
|---|---|---|
| 6,755,819 B1 | 6/2004 | Waelti |
| 2013/0085480 A1 | 4/2013 | Dick et al. |

(Continued)

FOREIGN PATENT DOCUMENTS

| | | | |
|---|---|---|---|
| DE | 10 2010 022 634 A1 | 12/2011 | |
| EP | 1153584 A1 * | 11/2001 | ........... A61B 3/0025 |

OTHER PUBLICATIONS

Bibi Safia Haq, Hidayat Ullah Khan, Khan Alam, Mian Mateenullah, Shehnaz Attaullah, and Islam Zari, "Femtosecond pulsed laser ablation of polyimide at oblique angles for medical applications," Appl. Opt. 54, 7413-7418 (2015) (Year: 2015).*

(Continued)

*Primary Examiner* — Benjamin J Klein
*Assistant Examiner* — Vynn V Huh
(74) *Attorney, Agent, or Firm* — MEDLER FERRO WOODHOUSE & MILLS PLLC

(57) ABSTRACT

A method for providing control data of an eye surgical laser of a treatment apparatus is disclosed for a treatment on a human or animal eye. The method optimizes a target conflict between low stress for a patient and efficacy of a laser. The method includes, as performed by a control device, determining a patient-specific parameter set, which relates to at least one physiological characteristic of the eye, determining at least one physical parameter for the eye surgical laser depending on the patient-specific parameter set, wherein the physical parameter relates to a physical characteristic of a laser beam of the laser, and providing control data for controlling the eye surgical laser, which includes the physical parameter.

13 Claims, 2 Drawing Sheets

(52) U.S. Cl.
CPC .............. *A61F 2009/00878* (2013.01); *A61F 2009/00885* (2013.01)

(58) Field of Classification Search
CPC ........ A61F 2009/00885; A61F 9/00804; A61F 9/00827; A61F 9/0084; A61F 9/00814; A61F 2009/00853; A61F 2009/00897; A61B 18/20–18/28; A61N 5/06–2005/073
USPC .................................................... 607/88–94
See application file for complete search history.

(56) References Cited

U.S. PATENT DOCUMENTS

| | | | | |
|---|---|---|---|---|
| 2015/0359602 | A1* | 12/2015 | Dai | G16H 50/50 606/4 |
| 2019/0175281 | A1* | 6/2019 | Dishler | A61F 9/00836 |
| 2019/0343683 | A1* | 11/2019 | Zheleznyak | A61F 9/00804 |

OTHER PUBLICATIONS

Arba-Mosquera, et al. "Influence of Extrinsic and Intrinsic Parameters on Myopic Correction in Small Incision Lenticule Extraction", Journal of Refractive Surgery, vol. 35, No. 11, 2019, doi.10.3926/1081597X-20191003-01, pp. 712-720.

* cited by examiner

METHOD FOR PROVIDING CONTROL DATA OF AN EYE SURGICAL LASER OF A TREATMENT APPARATUS BASED ON A PATIENT-SPECIFIC PARAMETER SET; CONTROL DEVICE AS WELL AS TREATMENT APPARATUS

FIELD

The present invention relates to a method for providing control data of an eye surgical laser of a treatment apparatus for a treatment on a human or animal eye, in particular on a cornea of the eye. A second aspect of the present invention relates to a control device, which is formed to perform the method. A third aspect of the present invention relates to a treatment apparatus with at least one eye surgical laser and the mentioned control device. Further aspects of the present invention relate to a computer program as well as to a computer-readable medium.

BACKGROUND

Treatment apparatuses and methods for controlling eye surgical lasers for the correction of optical visual disorders and/or pathologically and/or unnaturally altered areas of a cornea of a patient are known from the prior art. Therein, a pulsed laser and a beam device can for example be formed such that laser pulses effect a photodisruption and/or photoablation in a focus located within the organic tissue in order to remove a tissue, in particular a tissue lenticule, from the cornea. In this manner, a refractive power of the eye and the cornea, respectively, can be changed such that the capability of vision is improved for the corresponding patient. In order that a transition from the tissue to be removed to the cornea is not too abrupt, for example too steep, a transition area ("transition zone") is usually provided in the edge areas of the tissue to be removed, which provides a flattened transition for the tissue to be removed into the cornea.

Therein, today's systems and methods for example allow generic treatment approaches or those adapted to the respectively treated patient, which for example consider topographic information of the cornea or the respective patient or information on imaging errors and information on wavefronts, respectively (related to light incident on an eye of the respective patient). Thus, the mentioned adaptation to the respective patient exhausts itself in capturing and mapping, respectively, the surface of his eye and cornea, respectively, and in creating an ablation map adapted thereto.

In the treatment of the cornea or a corneal correction, there is always a target conflict between low stress for the patient and efficacy of the laser as high as possible, for example efficacy of the photoablation or photodisruption by the respective laser pulses of the laser. Thus, this poses an optimization problem.

SUMMARY

It is the object of the present invention to enable an improved solution of the optimization problem for a treatment of a patient and for a corneal correction, respectively.

According to the invention, this object is solved by the subject matters of the independent claims. Advantageous embodiments with convenient developments are the subject matter of the dependent claims.

The invention is based on the idea to adapt and adjust, respectively, physical characteristics of an eye surgical laser for the treatment of a cornea of a patient in patient-specific manner. Hereto, a patient-specific physical parameter can for example be determined for the eye surgical laser. By considering the patient-specific physical parameter in the operation of the laser, it can be operated in improved manner at the optimum of the mentioned optimization problem. Accordingly, the operation of the laser and the physical characteristics thereof, respectively, can be patient-specifically optimized to solve the target conflict between low stress for the patient and high efficacy in the photoablation and photodisruption, respectively, in improved manner.

The first aspect of the present invention claims a method for providing control data of an eye surgical laser of a treatment apparatus for a treatment on a human or animal eye, in particular a cornea of the eye, wherein the method comprises the following steps performed by a control device: determining a patient-specific parameter set, which relates to at least one physiological characteristic of the eye, determining at least one physical parameter for the eye surgical laser depending on the patient-specific parameter set, wherein the physical parameter relates to a physical characteristic of a laser beam of the laser, and providing control data for controlling the eye surgical laser, which includes the physical parameter; and providing control data for controlling the eye surgical laser, which includes the physical parameter.

Determining the patient-specific parameter set can include determining one or multiple patient-specific parameters. The one or the multiple patient-specific parameters, which collectively constitute the patient-specific parameter set, can each individually or collectively relate to the physiological characteristic of the eye. Exemplary physiological characteristics of the eye, which can be described by the patient-specific parameter set, are a reflectivity of a surface of the eye, a moisture content of the eye, a size and a diameter, respectively, or a radius of an already present or planned optical zone of the eye, a degree of myopia or hyperopia, an age of the patient, a sensitivity of a tissue of the eye and the cornea, respectively, with respect to a laser pulse and/or the like. One or more of the mentioned exemplary physiological characteristics of the eye can be characterized and quantified, respectively, by the patient-specific parameter set. Each one physiological characteristic of the eye, for example one of the exemplarily mentioned ones and/or a different one, can each be characterized and quantified, respectively, by one or multiple patient-specific parameters.

The at least one physical parameter for the eye surgical laser is determined depending on the patient-specific parameter set. The at least one physical parameter can for example be determined based on or considering the one patient-specific parameter or the multiple patient-specific parameters. Based on the at least one physical parameter, an operation of the eye surgical laser can be adapted in patient-specific manner, thus in particular to the at least one physiological characteristic of the eye. For example, the operation of the eye surgical laser can be adapted to one or more of the physiological characteristics of the eye exemplarily enumerated above. The physical characteristic of the laser beam of the laser can be preset by corresponding specification of the at least one physical parameter. In other words, at least one physical characteristic of the laser beam of the laser is dependent on the physical parameter. Thus, the physical characteristic of the laser beam can be patient-specifically adapted to the eye.

By providing the control data, which includes the physical parameter, the eye surgical laser can be controlled or influenced depending on the physical parameter. In particular, the physical characteristic of the laser can be adjusted or preset corresponding to the at least one physical parameter depending on the control data. For example, adjusting the eye surgical laser can be dependent on the physical parameter and the control data part of the present method, respectively. In this case, adjusting can for example be performed by the same control device, by which the remaining described method steps are performed. Alternatively, it can be provided that the eye surgical laser is controlled and adjusted, respectively, by a different control device. In this case, providing the control data can for example be effected via a corresponding interface to the different control device. The control data, which includes the physical parameter, can then be transmitted or communicated to the different control device via the interface.

Overall, the invention has the advantage that the laser beam of the laser can be physically adapted to the patient and his eye, respectively, by determining the patient-specific parameter set as well as the at least one physical parameter. Hereby, a patient-specific optimum of the initially described target conflict between stress of the patient as low as possible and high efficacy of the photoablation and the photodisruption, respectively, can be adjusted or preset by corresponding influence of the laser beam. Thus, an optimum ratio of high efficacy of the laser beam and low stress of the patient by the laser beam can be determined and adjusted in patient-specific manner.

According to a development, the method comprises the following additional steps of providing a patient-unspecific parameter set, which is based on a cross-section of a plurality of patients and includes at least one standard value for the at least one physiological characteristic of the eye; and determining a deviation between the patient-unspecific parameter set and the patient-specific parameter set, wherein determining the at least one physical parameter is effected at least depending on the previously determined deviation.

The patient-unspecific parameter set can include an average value for the at least one physiological characteristic of the eye for the plurality of patients as the standard value. Of course, the patient-unspecific parameter set can include a respective or multiple respective standard values for different or multiple physiological characteristics. Therein, the standard value can present or represent an average value, a median value, an accumulation value or any other value, which describes the plurality of patients on average. In other words, the at least one physiological characteristic of the eye in cross-section of the plurality of patients can be described by the standard value. In case of multiple standard values, which are part of the patient-unspecific parameter set, each of the standard values can relate to and describe, respectively, a respective physiological characteristic of the eye in cross-section of the plurality of patients. Since the standard value or standard values is/are related to a plurality of patients, the designation is effected as patient-unspecific. In contrast thereto, the patient-specific parameter set is specific to a respective patient.

In determining the deviation between the patient-unspecific parameter set and the patient-specific parameter set, it can be determined how far the patient-specific parameter deviates from the standard value. In case of multiple patient-specific parameters, it can be determined how far the patient-specific parameters deviate from the respective standard value for the same physiological characteristic of the eye. In this manner, the deviation can specify, how severely the at least one physiological characteristic of the eye coincides with the cross-section of the plurality of patients. Determining the physical parameter for the eye surgical laser is then determined depending on the deviation. Therein, the deviation can be represented by a single numerical value or by a matrix or the like. For example, a standard value can be preset or get preset for the physical parameter. Determining the physical parameter depending on the deviation can then be effected such that the at least one physical parameter is derived from the standard value for the corresponding physical parameter depending on the deviation between the patient-unspecific parameter set and the patient-specific parameter set. In this manner, both the manifestation of the physiological characteristic usual across many patients and the patient-specific manifestation of the physiological characteristic can be taken into account in particularly advantageous manner.

According to a development, it is provided that determining the at least one physical parameter is effected based on a model of the eye, which is adapted to the patient based on the patient-specific parameter set starting from a basic model. For example, the basic model can be adapted to the patient considering at least one patient-specific parameter and/or by adaptation based on at least one patient-specific parameter. Thus, a patient-specific model is derived from the basic model depending on the patient-specific parameter set. Such a model is amenable to a simulation and optimization, respectively, with respect to the at least one physical parameter in particular manner. Based on such a derived patient-specific model, thus, the optimization of the physical characteristic of the laser beam can be adapted to the patient to a particular degree.

According to a development, it is provided that a respectively different model is used for determining the at least one physical parameter depending on a type of a planned treatment on the eye. In particular, a respectively different basic model is provided for different treatments on the eye. Depending on the planned treatment on the eye, a basic model specific to the respective treatment can be selected from multiple basic models and adapted to the patient. The different models and different basic models, respectively, for different types of the treatment can each consider different influencing factors, different patient-specific parameters and/or physiological characteristics of the eye. Thus, the model is adapted to the treatment respectively to be performed to a particular degree.

According to a development, it is provided that a respective value for a wavelength and/or a pulse duration and/or a pulse energy is determined as the at least one physical parameter. In other words, the physical parameter can preset a wavelength for the laser beam. Alternatively, or additionally, the physical parameter can preset a pulse duration for the laser beam. Alternatively, or additionally, the physical parameter can preset a pulse energy for the laser beam. In still other words, the at least one physical parameter can preset a respective value for one or multiple of the exemplarily mentioned physical quantities and physical characteristics of the laser beam, respectively. In this manner, it is taken into account that the mentioned quantities each can have a particularly advantageous influence on the initially mentioned target conflict.

According to a development, it is provided that determining the at least one physical parameter is effected depending on an angle of incidence of the laser beam on a surface of the eye. Therein, it can in particular be provided that the flatter the angle of incidence, the greater the pulse energy. Conversely, the steeper the angle of incidence is, the smaller the pulse energy can be. In other words, depending on the angle of incidence, the laser beam pulse energy can have a minimum with a perpendicular angle of incidence on the surface of the eye or the cornea.

In further configuration, it can be provided that the angle of incidence of the laser beam is derived based on a size of an optical zone to be generated by the treatment. In this manner, it can be taken into account that the angle of incidence becomes increasingly flat with increasing size of the optical zone. In this manner, a correlation between the size of the optical zone and the pulse energy of the laser beam can arise. Therein, the pulse energy is advantageously the greater, the larger the optical zone is.

Overall, by the dependency between pulse energy and angle of incidence, it can be taken into account that a greater portion of the laser pulse is reflected by the eye with flatter angles of incidence. Thus, a lower portion of the laser pulse or the laser beam would be of use for the treatment with the same pulse energy and larger angle of incidence. By the portion of the laser beam or the laser pulse reflected by the eye, a contribution to the treatment success of the treatment cannot be made. This can be taken into account or compensated for by the present automatic increase of the pulse energy depending on the angle of incidence and the size of the optical zone, respectively. The pulse energy is in particular the entire energy, which is emitted by the laser beam during a laser pulse. Therein, it is to be noticed that the laser, as was already initially described, is operated in pulsed manner. Thus, the pulse energy can be the integral over the energy of a pulse.

According to a development, it is provided that a value with respect to a moisture content of the eye is determined as the at least one physiological characteristic of the eye. Therein, it is in particular provided that an all the higher pulse energy is determined, the greater the moisture content of the eye represented by the value is. In other words, the pulse energy can be all the greater, the greater the moisture content of the eye represented by the value is. The value with respect to the moisture content of the eye can be a parameter of the patient-specific parameter set. For example, the moisture content of the eye can be measured by a corresponding capturing device for measuring the moisture content of the eye. Alternatively, or additionally, the moisture content of the eye can for example be determined or estimated based on an image of the eye, for instance a digital photograph of the eye, by a corresponding algorithm. Alternatively, or additionally, the value with respect to the moisture content of the eye can be derived or determined from a user input, for instance via a corresponding input appliance connected to the control device. Alternatively, or additionally, the moisture content or the value can be derived from an age of the patient. This is based on the realization that the moisture content of the eye usually increases with increasing age of the patient. In further configuration, the value with respect to the moisture content of the eye can also be an age statement with respect to the patient. In this case, the moisture content of the eye can be represented based on the age or by the age statement. This in particular means that the pulse energy of the laser beam is selected the higher, the older the patient is. In sum, the value with respect to the moisture content of the eye can be based on a measurement, an image-assisted estimation by an algorithm, a user statement and/or an age statement of the patient. Of course, combinations of the enumerated possibilities for determining the value with respect to the moisture content are also possible. The value with respect to the moisture content of the eye can specify the moisture content or information correlated with the moisture content of the eye, for instance the age of the patient. Hereby, it can overall be taken into account that a higher pulse energy is required with increasing moisture content of the eye to ensure a preset ablation efficiency and efficiency in the photodisruption, respectively.

According to a development, it is provided that the pulse energy is determined depending on a refraction to be corrected by the treatment. Therein, it can in particular be provided that in case of the treatment of myopia, an all the smaller pulse energy is determined, the greater the refraction to be corrected is. Alternatively, or additionally, it can be provided that in case of the treatment of hyperopia, an all the greater pulse energy is determined, the greater the refraction to be corrected is. In other words, the pulse energy can be determined depending on the visual disorder of the patient to be corrected. However, therein, it optimally depends on the type of the respective visual disorder. Thus, depending on the type of the respective visual disorder, thus for example either myopia or hyperopia, the pulse energy can increase or decrease with increasing visual disorder or refraction to be corrected. In case of the treatment of myopia, the pulse energy is selected the smaller, the greater the refraction or visual disorder to be corrected is. Conversely, in case of a treatment of myopia, an all the greater pulse energy can be determined, the lower or the smaller the refraction or visual disorder to be corrected is. In case of the treatment of the hyperopia, the correlation between pulse energy and refraction to be corrected is preferably inverse. In case of the treatment of hyperopia, the pulse energy can be determined the greater, the greater the refraction or visual disorder to be corrected is. Conversely, in case of the treatment of the hyperopia, the pulse energy can be selected the smaller, the smaller or the lower the refraction or visual disorder to be corrected is. In this manner, an optimum efficacy of the treatment with low invasiveness at the same time can be ensured in patient-specific manner according to visual disorder of the patient.

According to a development, it is provided that the pulse energy is predominantly adapted in patient-specific manner in case of ablation and/or the pulse duration is predominantly adapted in patient-specific manner in case of photodisruption. In other words, the variable dominant in case of the ablation for patient-specific adaptation of the laser beam can be the pulse energy. Alternatively, or additionally, in case of photodisruption or bubble formation, the dominant variable for adapting the laser beam to the patient can be the pulse duration. For example, in case of the photoablation or ablation, the pulse energy can have a greater variation range or range of values than in case of a photodisruption or bubble formation. Alternatively, or additionally, the pulse duration can have a greater variation range or range of values in case of the photodisruption or bubble formation than in case of the ablation or photoablation. In this manner, a respectively even better adaptation to the patient can be allowed depending on the type of the treatment respectively to be performed.

A second aspect of the present invention relates to a control device, which is configured to perform one of the above described methods. The above cited advantages arise. For example, the control device can be configured as a control chip, control appliance or application program ("app"). Preferably, the control device can comprise a processor device and/or a data storage. An appliance or an appliance component for electronic data processing is understood by a processor device. For example, the processor device can comprise at least one microcontroller and/or at least one microprocessor. Preferably, a program code for performing the method according to the invention can be stored on the optional data storage. The program code can then be configured, upon execution by the processor device, to cause the control device to perform one of the above described embodiments of one or both methods according to the invention.

A third aspect of the present invention relates to a treatment apparatus with at least one eye surgical laser for the separation of a tissue predefined by the control data, in particular of a corneal volume with predefined interfaces of a human or animal eye by means of photodisruption and/or photoablation, and at least one control device for the laser or lasers, which is formed to execute the steps of the method according to the first aspect of the invention. The treatment apparatus according to the invention allows that the disadvantages occurring in the use of usual ablative treatment apparatuses are reliably reduced or even avoided.

In a further advantageous configuration of the treatment apparatus according to the invention, the laser can be suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kilohertz (kHz), preferably between 100 kHz and 100 megahertz (MHz). Such a femtosecond laser is particularly well suitable for removing tissue within the cornea. The use of photodisruptive and/or photoablative lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is allowed. In particular, the range between 700 nm and 780 nm can also be selected as the wavelength range.

In further advantageous configurations of the treatment apparatus according to the invention, the control device can comprise at least one storage device for at least temporary storage of at least one control dataset, wherein the control dataset or datasets include(s) control data for positioning and/or for focusing individual laser pulses in the cornea; and can comprise at least one beam device for beam guidance and/or beam shaping and/or beam deflection and/or beam focusing of a laser beam of the laser. Therein, the mentioned control dataset includes the control data determined in the method for removing the tissue.

Further features and the advantages thereof can be taken from the descriptions of the first inventive aspect, wherein advantageous configurations of each inventive aspect are to be regarded as advantageous configurations of the respectively other inventive aspect.

A fourth aspect of the invention relates to a computer program including commands, which cause the treatment apparatus according to the third inventive aspect to execute the method steps according to the first inventive aspect.

A fifth aspect of the invention relates to a computer-readable medium, on which the computer program according to the fourth inventive aspect is stored. Further features and the advantages thereof can be taken from the descriptions of the first to fourth inventive aspects, wherein advantageous configurations of each inventive aspect are to be regarded as advantageous configurations of the respectively other inventive aspect.

BRIEF DESCRIPTION OF DRAWINGS

Further features of the invention are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims. There show:

DETAILED DESCRIPTION

Figure 1:
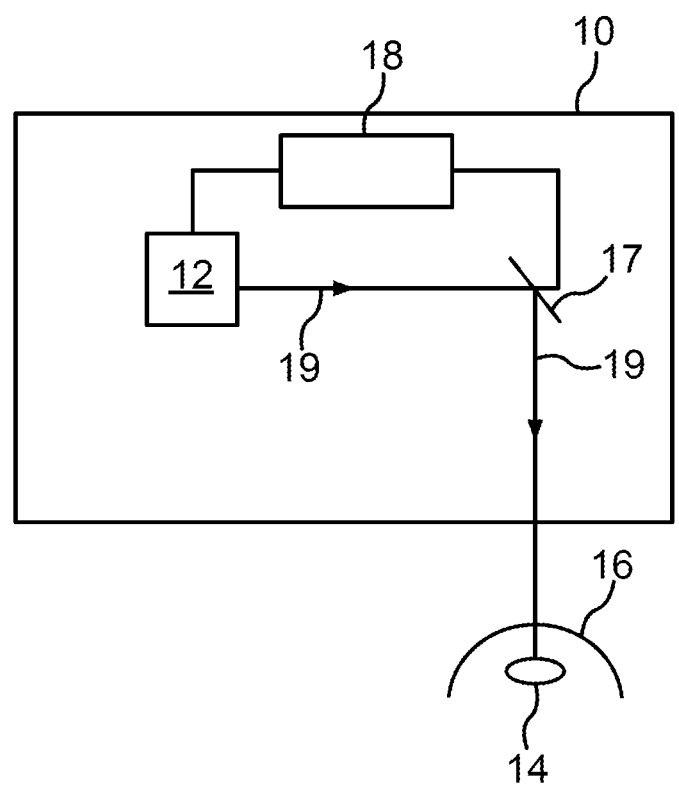
FIG. 1 a schematic representation of a treatment apparatus according to the invention according to an exemplary embodiment.

FIG. 1 shows a schematic representation of a treatment apparatus 10 with an eye surgical laser 12 for the removal of a tissue 14 of a human or animal eye 16 by means of photodisruption and/or photoablation. For example, the tissue 14 can represent a lenticule or also volume body, which can be separated from a cornea of the eye 16 for correcting a visual disorder by the eye surgical laser 12. A geometry of the tissue 14 to be removed, thus a tissue removal geometry 14, can be provided by a control device 18, in particular in the form of control data, such that the laser 12 emits pulsed laser pulses in a pattern predefined by the control data into the cornea of the eye 16 to remove the tissue 14. Alternatively, the control device 18 can be a control device 18 external with respect to the treatment apparatus 10.

Furthermore, FIG. 1 shows that the laser beam 19 generated by the laser 12 can be deflected towards the eye 16 by means of a beam deflection device 22, namely a beam deflection apparatus such as for example a rotation scanner, to remove the tissue 14. The beam deflection apparatus 22 can also be controlled by the control device 18 to remove the tissue 14.

Preferably, the illustrated laser 12 can be a photodisruptive and/or photoablative laser, which is formed to emit laser pulses in a wavelength range between 300 nanometers and 1400 nanometers, preferably between 700 nanometers and 1200 nanometers, at a respective pulse duration between 1 femtosecond and 1 nanosecond, preferably between 10 femtoseconds and 10 picoseconds, and a repetition frequency of greater than 10 kilohertz, preferably between 100 kilohertz and 100 megahertz. Optionally, the control device 18 additionally comprises a storage device (not illustrated) for at least temporary storage of at least one control dataset, wherein the control dataset or datasets include(s) control data for positioning and/or for focusing individual laser pulses in the cornea. The position data and/or focusing data of the individual laser pulses, that is the tissue removal geometry 14, are ascertained based on the method described below.

Figure 2:
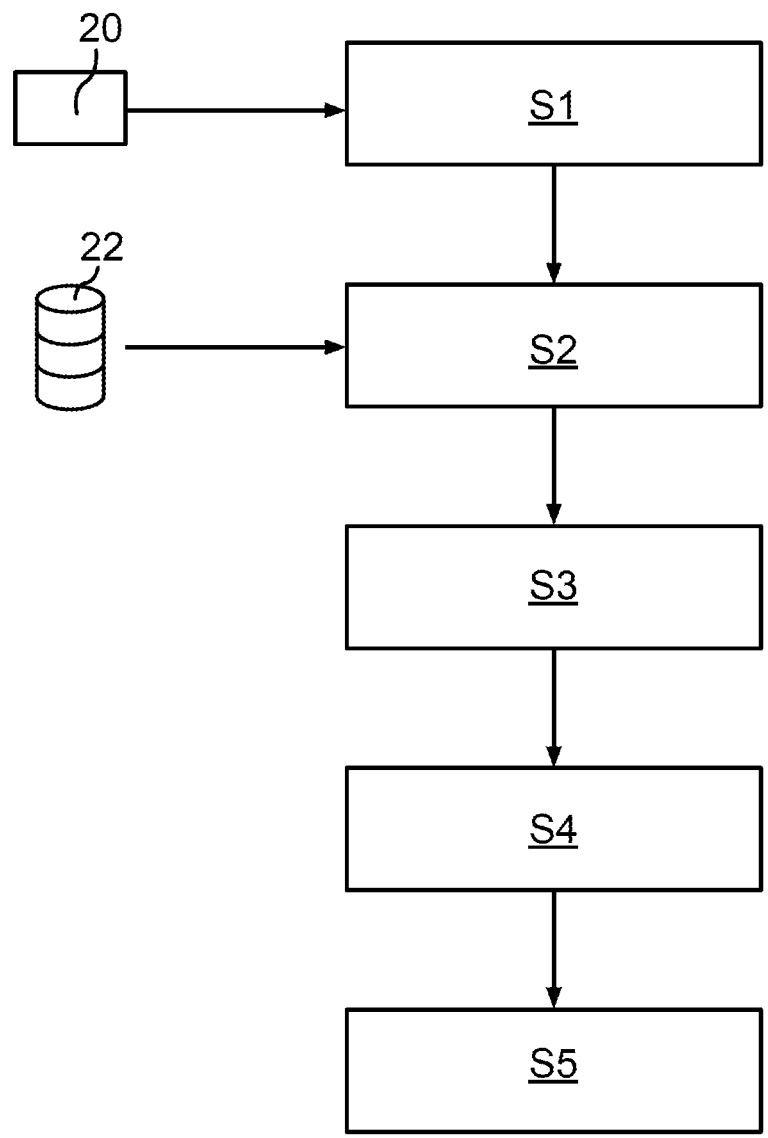
FIG. 2 a flow diagram of a method according to the invention according to an exemplary embodiment.

FIG. 2 shows a flow diagram of an exemplary embodiment of a method for providing control data of the eye surgical laser 12 of the treatment apparatus 10. Therein, the control data of the eye surgical laser 12 of the treatment apparatus 10 is determined for a corneal correction depending on an externally determined correction value. Based on the control data, thus, the corneal correction can be performed. In other words, the eye surgical laser 12 and the treatment apparatus 10, respectively, perform the corresponding corneal correction determined depending on the correction value in a control according to the control data generated by means of the method.

Therein, the method exemplarily comprises the following steps performed by the control device 18: Step S1: Determining a patient-specific parameter set, which relates to at least one physiological characteristic of the eye 16, Step S2: Providing S2 a patient-unspecific parameter set, which is based on a cross-section of a plurality of patients and includes at least one standard value for the at least one physiological characteristic of the eye 16, and Step S3: Determining a deviation between the patient-unspecific parameter set and the patient-specific parameter set, Step S4: Determining at least one physical parameter for the eye surgical laser 12 depending on the patient-specific parameter set, wherein the physical parameter relates to a physical characteristic of a laser beam 19 of the laser 12, wherein determining the at least one physical parameter is effected at least depending on the deviation, and Step S5: Providing control data for controlling the eye surgical laser 12, which includes the physical parameter.

Determining the patient-specific parameter set can include determining one or multiple patient-specific parameters. The one or the multiple patient-specific parameters are presently determined by a determination apparatus 20. The determination apparatus 20 can be a part of the treatment apparatus 10 and/or a part of the control device 18. The one or the multiple patient-specific parameters each individually or collectively relate to one or multiple physiological characteristics of the eye 16. Exemplary physiological characteristics of the eye 16, which can be described by the patient-specific parameter set, are a reflectivity of a surface of the eye, a moisture content of the eye 16, a size and a diameter, respectively, or a radius of an already present or planned optical zone of the eye, a degree of myopia or hyperopia, an age of the patient, a sensitivity of a tissue of the eye or the cornea with respect to a laser pulse and/or the like.

For example, the determination apparatus 20 can comprise a measurement unit for measuring or estimating the moisture content of the eye 16. Alternatively, the moisture content of the eye 16 can be derived or estimated at least from the age of the patient. This can be effected based on a predetermined formula. For example, the age of the patient can be derived from a user input of a user, in particular a physician. The user input can be received by the determination apparatus 20 for example from a patient database or an input appliance. Calculations underlying hereto can for example be performed by a microprocessor, a digital signal processor (DSP), an FPGA or the like of the determination apparatus 20 and/or control unit 18.

Size and/or diameter and/or radius of the planned optical zone for the eye 16 can for example be derived from ablation data and/or photodisruption data. Based on the ablation data and/or photodisruption data, the refraction to be corrected by the treatment can additionally be determined. Similarly, it can be determined if the visual disorder to be corrected is myopia or hyperopia. The ablation data and photodisruption data, respectively, describe and quantify, respectively, a presently planned ablation and photodisruption, respectively, for correcting the refraction or the visual disorder (thus for example the myopia or hyperopia). The ablation data can for example be an ablation map. In the present example, it is provided that determining the at least one physical parameter is effected depending on an angle of incidence of the laser beam 19 on a surface of the eye 16. The angle of incidence of the laser beam 19 can be derived from the size and/or the diameter and/or the radius of the planned optical zone for the eye 16. Therein, a flatter angle of incidence usually results from a larger optical zone. Calculations underlying hereto can for example be performed by the microprocessor, the digital signal processor (DSP), the FPGA or the like of the determination apparatus 20 and/or control unit 18.

The patient-unspecific parameter set can include an average value for the at least one physiological characteristic of the eye for the plurality of patients as the standard value. For example, the patient-unspecific parameter set can be retrieved from a model database 22. Of course, the patient-unspecific parameter set can include a respective or multiple respective standard values for different or multiple physiological characteristics. Therein, the standard value can present or represent an average value, a median value, an accumulation value or any other value describing the plurality of patients on average. In other words, the at least one physiological characteristic of the eye in cross-section of the plurality of patients can be described by the standard value. In case of multiple standard values, which are part of the patient-unspecific parameter set, each of the standard values can relate to or describe a respective physiological characteristic of the eye in cross-section of the plurality of patients. Since the standard value or the standard values is/are related to a plurality of patients, the designation is effected as patient-unspecific. In contrast thereto, the patient-specific parameter set is specific to a respective patient.

In determining the deviation between the patient-unspecific parameter set and the patient-specific parameter set, it can be determined how far the patient-specific parameters deviate from the respective standard value for the same physiological characteristic of the eye. In this manner, the deviation can specify, how severely the at least one physiological characteristic of the eye coincides with the cross-section of the plurality of patients. Therein, the deviation can be represented by a single numerical value or by a matrix or the like.

The model database 22 can contain one or multiple biophysical models of an eye. Based on the patient-specific parameter set, the respective model can be adapted to the individual patient. In other words, the respective model can be parameterizable based on the parameters of the patient-specific parameter set. Thereby, a deviation between a standard basic model and the patient-specific parametrized model can be determined on the one hand. This deviation can be used for determining a patient-specific adaptation starting from the standard basic model alternatively or additionally to the above mentioned deviation between the patient-unspecific parameter set and the patient-specific parameter set. The standard basic model can for example be parameterized by the patient-unspecific parameter set. Alternatively, or additionally, the patient-specifically parametrized model can be used to simulate an influence of the physical parameter and of patient-specific adaptations of the physical parameter, respectively.

Therein, it is in particular provided that depending on a type of the planned treatment on the eye 16, a respectively different model is applied or used. In particular, a respectively different basic model is provided for different treatments on the eye 16. Depending on the planned treatment on the eye, a basic model specific to the respective treatment can be selected from multiple basic models and adapted to the patient corresponding to the above mentioned parameterization. The different models or different basic models for different types of the treatment can each consider different influencing factors, different patient-specific parameters and/or physiological characteristics of the eye. Thus, the model is adapted to the treatment respectively to be performed to a particular degree.

For example, the physical parameter can be determined starting from a standard value. For example, the standard value can be preset or get preset for the physical parameter. The patient-specific determination of the physical parameter depending on the deviation can then be effected such that the at least one physical parameter is derived from the standard value for the corresponding physical parameter depending on the deviation between the patient-unspecific parameter set and the patient-specific parameter set and/or the deviation between the standard model and the patient-specifically parameterized model.

Presently, a wavelength as well as a pulse duration and a pulse energy are determined as the respective physical parameter. In other words, the physical parameter can preset the wavelength for the laser beam 19. Alternatively, or additionally, the physical parameter can preset the pulse duration for the laser beam 19. Alternatively, or additionally, the physical parameter can preset the pulse energy for the laser beam 19.

Presently, the determination of the physical parameter, in particular of the pulse energy, is effected depending on the angle of incidence of the laser beam 19 on a surface of the eye 16. Therein, it can in particular be provided that the pulse energy is the greater, the flatter the angle of incidence is. Conversely, the pulse energy can be the smaller, the steeper the angle of incidence is. As described above, the angle of incidence of the laser beam 19 is derived based on the size of the optical zone to be generated by the treatment. In this manner, it can be taken into account that the angle of incidence becomes increasingly flatter with increasing size of the optical zone. In this manner, a correlation between the size of the optical zone and the pulse energy of the laser beam can arise. Therein, the pulse energy is advantageously the greater, the larger the optical zone is.

Presently, the determination of the physical parameter, in particular of the pulse energy, is effected depending on the moisture content of the eye 16. Therein, it is in particular provided that an all the higher pulse energy is determined, the greater the moisture content of the eye is. Alternatively, or additionally, the moisture content or the value can be derived from the age of the patient. This is based on the realization that the moisture content of the eye usually increases with increasing age of the patient. The moisture content of the eye can be derived based on the age or represented by the age statement. This in particular means that the pulse energy of the laser beam is selected the higher, the older the patient is.

Presently, the determination of the physical parameter, in particular of the pulse energy, is effected depending on the refraction to be corrected by the treatment. Therein, it can in particular be provided that in case of the treatment of myopia, an all the smaller pulse energy is determined, the greater the refraction to be corrected is. Alternatively, or additionally, it can be provided that in case of the treatment of hyperopia, an all the greater pulse energy is determined, the greater the refraction to be corrected is.

Overall, it is shown by the embodiment, how the treatment can be adapted to the patient in automated manner to a high degree. Thereby, a particularly high efficiency of the treatment can be particularly well associated with a stress for the patient as low as possible.

LIST OF REFERENCE CHARACTERS

10 Treatment apparatus
12 laser
14 tissue
16 eye
17 beam deflection device
18 control device
19 laser beam
20 determination apparatus
22 model database
S1 . . . S5 method steps

What is claimed is:

1. A method for providing control data of an eye surgical laser of a treatment apparatus for a photoablation or photodisruption treatment on a human or animal eye, wherein the method comprises the following steps performed by a control device:

determining a patient-specific parameter set, which relates to at least one physiological characteristic of the human or animal eye;

determining at least one physical parameter for the eye surgical laser depending on the patient-specific parameter set, wherein the at least one physical parameter relates to a physical characteristic of a laser beam of the eye surgical laser; and providing control data for controlling the eye surgical laser, which includes the at least one physical parameter;

wherein a respective value for a wavelength and/or a pulse duration and/or a pulse energy is determined as the at least one physical parameter; and the pulse energy is determined depending on a refraction to be corrected by the treatment, wherein in the treatment of myopia, when the refraction to be corrected is increased, the pulse energy is decreased based on dependency between pulse energy and angle of incidence of the laser beam, and/or in the treatment of hyperopia, when the refraction to be corrected is increased, the pulse energy is increased based on the dependency between the pulse energy and the angle of incidence of the laser beam.

2. The method according to claim 1, further including the steps of:

providing a patient-unspecific parameter set, which is based on a cross-section of a plurality of patients and includes at least one standard value for the at least one physiological characteristic of the human or animal eye; and determining a deviation between the patient-unspecific parameter set and the patient-specific parameter set, wherein determining the at least one physical parameter is affected at least depending on the deviation.

3. The method according to claim 1, wherein determining the at least one physical parameter is affected based on a model of the human or animal eye, which is adapted to a patient based on the patient-specific parameter set starting from a basic model.

4. The method according to claim 3, wherein depending on a type of a planned treatment on the human or animal eye, a respectively different model for determining the at least one physical parameter is used.

5. The method according to claim 1, wherein determining the at least one physical parameter is affected depending on the angle of incidence of the laser beam on a surface of the human or animal eye, wherein the pulse energy is increased when the angle of incidence is flatter.

6. The method according to claim 1, wherein a value with respect to a moisture content of the human or animal eye is determined as the at least one physiological characteristic of the human or animal eye, and wherein the pulse energy is increased when the moisture content of the human or animal eye represented by the value is increased.

7. The method according to claim 1, wherein in case of an ablation, the pulse energy is predominantly patient-specifically adapted, and/or in case of a photodisruption, the pulse duration is predominantly patient-specifically adapted.

8. A control device, which is formed to perform the method according to claim 1.

9. A treatment apparatus with at least one eye surgical laser for performing a corneal correction on a cornea by the control device according to claim 8.

10. The treatment apparatus according to claim 9, wherein the eye surgical laser is formed to emit laser pulses in a wavelength range between 300 nm and 1400 nm, at a respective pulse duration between 1 fs and 1 ns, and a repetition frequency of greater than 10 kHz.

11. The treatment apparatus according to claim 9, wherein the control device comprises at least one storage device for at least temporary storage of at least one control dataset, wherein the at least one control dataset includes control data for positioning and/or focusing individual laser pulses in the cornea; and
    includes at least one beam device for beam guidance and/or beam shaping and/or beam deflection and/or beam focusing of the laser beam of the eye surgical laser.

12. The treatment apparatus according to claim 9, wherein the eye surgical laser is formed to emit laser pulses in a wavelength range between 700 nm and 1200 nm, at a respective pulse duration of between 10 fs and 10 ps, and a repetition frequency of between 100 kHz and 100 MHz.

13. A computer-readable medium having stored thereon a computer program including commands, the computer program which causes the treatment apparatus with the eye surgical laser to perform a corneal correction on a cornea by the control device to execute the method according to claim 1.

* * * * *

UNITED STATES PATENT AND TRADEMARK OFFICE
CERTIFICATE OF CORRECTION

| | | |
|---|---|---|
| PATENT NO. | : 12,396,888 B2 | Page 1 of 1 |
| APPLICATION NO. | : 17/562185 | |
| DATED | : August 26, 2025 | |
| INVENTOR(S) | : Samuel Arba Mosquera et al. | |

It is certified that error appears in the above-identified patent and that said Letters Patent is hereby corrected as shown below:

In the Claims

Column 12, Claim 1, Line 49: "based on dependency between pulse energy and angle" corrected to -- based on a dependency between the pulse energy and angle --.

Signed and Sealed this
Thirtieth Day of September, 2025

John A. Squires
*Director of the United States Patent and Trademark Office*